United States Patent
Shibata et al.

(10) Patent No.: US 8,804,112 B2
(45) Date of Patent: Aug. 12, 2014

(54) METHOD OF DEFECT INSPECTION AND DEVICE OF DEFECT INSPECTION

(75) Inventors: Yukihiro Shibata, Fujisawa (JP); Toshihiko Nakata, Hiratsuka (JP); Taketo Ueno, Kawasaki (JP); Atsushi Taniguchi, Fujisawa (JP); Toshifumi Honda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 249 days.

(21) Appl. No.: 13/265,935

(22) PCT Filed: Apr. 22, 2010

(86) PCT No.: PCT/JP2010/057164
§ 371 (c)(1),
(2), (4) Date: Dec. 7, 2011

(87) PCT Pub. No.: WO2010/123074
PCT Pub. Date: Oct. 28, 2010

(65) Prior Publication Data
US 2012/0092657 A1 Apr. 19, 2012

(30) Foreign Application Priority Data

Apr. 24, 2009 (JP) .................................. 2009-105913

(51) Int. Cl.
*G01N 21/00* (2006.01)
(52) U.S. Cl.
USPC ....................................................... 356/237.4
(58) Field of Classification Search
CPC ................... G01N 21/84–21/958; G01N 21/00
USPC ....................................................... 356/237.4
See application file for complete search history.

(56) References Cited

U.S. PATENT DOCUMENTS

| 7,037,735 | B2* | 5/2006 | Noguchi et al. | 438/18 |
| 7,098,055 | B2* | 8/2006 | Noguchi et al. | 438/18 |
| 2006/0030059 | A1* | 2/2006 | Noguchi et al. | 438/7 |
| 2007/0146696 | A1* | 6/2007 | Noguchi et al. | 356/237.5 |
| 2007/0146697 | A1* | 6/2007 | Noguchi et al. | 356/237.5 |
| 2008/0297783 | A1* | 12/2008 | Urano et al. | 356/237.5 |
| 2009/0141269 | A1* | 6/2009 | Uto et al. | 356/237.2 |
| 2010/0106443 | A1* | 4/2010 | Shimura et al. | 702/81 |

FOREIGN PATENT DOCUMENTS

| JP | 2007-232555 | 9/2007 |
| JP | 2008-58111 | 3/2008 |
| JP | 2008-268141 | 11/2008 |
| WO | WO 03/069263 A2 | 8/2003 |

\* cited by examiner

*Primary Examiner* — Roy M Punnoose
(74) *Attorney, Agent, or Firm* — Antonelli, Terry, Stout & Kraus, LLP.

(57) ABSTRACT

A method of inspecting defects and a device inspecting defects of detecting defects at high sensitivity and high capture efficiency even on various patterns existing on a wafer. In the device of inspecting defects, an illumination optical system is formed of two systems of a coherent illumination of a laser 5 and an incoherent illumination of LEDs 6a, 6b, 6c and 6d, and light paths are divided in a detecting system corresponding to respective illumination light, spatial modulation elements 55a and 55b are arranged to detecting light paths, respectively, scattered light inhibiting sensitivity is shielded by the spatial modulating elements 55a and 55b, scattered light transmitted through the spatial modulation elements 55a and 55b is detected by image sensors 90a and 90b arranged to respective light paths, and images detected by these two image sensors 90a and 90b are subjected to a comparison processing, thereby determining a defect candidate.

8 Claims, 6 Drawing Sheets

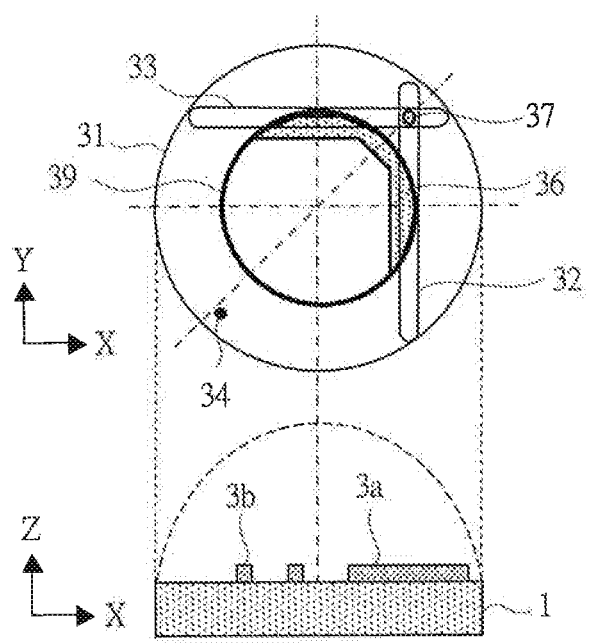
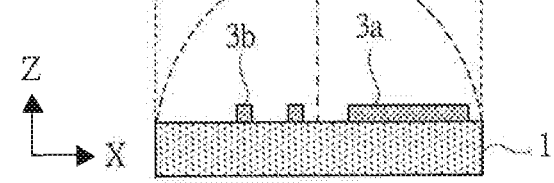

FIG. 7
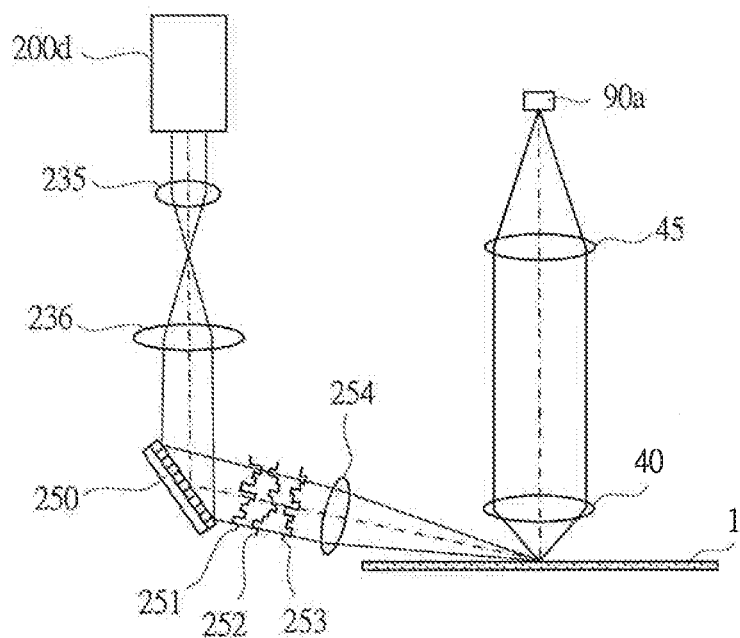
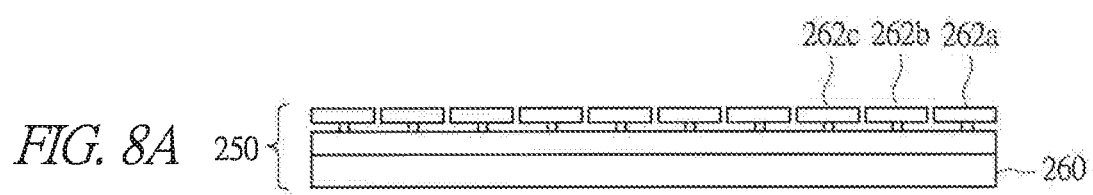
FIG. 8A
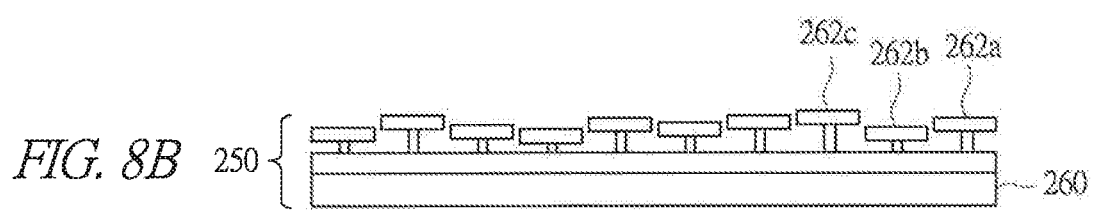
FIG. 8B

METHOD OF DEFECT INSPECTION AND DEVICE OF DEFECT INSPECTION

BACKGROUND OF THE INVENTION

The present invention relates to a method of inspecting defects and a device of inspecting defects for inspecting defects of a fine pattern formed on a wafer after a thin-film process represented by a semiconductor manufacturing process and a manufacturing process of a flat panel display.

An existing semiconductor inspecting device is described in Patent Document 1 (WO2003/069263). The inspecting device mounts a dark field detection optical system which detects scattered light on a wafer by illuminating a surface of the wafer from a tilted direction by laser light. Diffracted light from a cyclic pattern is shielded by a spatial filter arranged at a back focus position (exit pupil position) of an objective lens in this optical system.

PRIOR ART DOCUMENT

Patent Document

Patent Document 1: WO2003/069263

SUMMARY OF THE INVENTION

Problems to be Solved by the Invention

Various patterns are formed on a wafer, and there are various kinds of defects depending on causes of generating the defects. In patterns represented by DRAM (Dynamic Random Access Memory) etc., wirings of cyclic patterns are formed and it is possible to shield diffracted light from a cyclic pattern by a spatial filter.

However, a non-cyclic pattern exists on a water like a logic computing unit (logic portion). Scattered light of the non-cyclic pattern is scattered to regions different from the cyclic pattern by a Fourier transform plane of the objective lens.

Further, scattered light from a logic pattern of the logic computing portion is not distributed in a dotted manner as a memory portion but spread widely, and thus it is impossible to shield all the scattered light from the pattern. Therefore, to inspect a semiconductor mounting a memory and a logic together with a high sensitivity, there have been the following problems.

(1) It is necessary to set different spatial filters to the memory portion and the logic portion.

(2) Since it is impossible to completely shield scattered light from the pattern in the logic portion, fluctuations in brightness of a pattern image is a cause of inhibiting inspection sensitivity. Therefore, it is necessary to stably detecting a logic pattern image.

(3) As the pattern is detected brighter in the logic portion than the memory portion, when an image is detected with constant illumination light, brightness of the logic portion reaches a saturation level of an optical detector with respect to the memory portion, and thus the logic portion is practically uninspected.

Accordingly, the present invention is provides a method of inspecting defects and a device of inspecting defects for detecting defects on various kinds of patterns existing on a wafer with high sensitivity and high capture efficiency.

These and other objects, features and advantages of the invention will be apparent from the following more particular description of preferred embodiments of the invention, as illustrated in the accompanying drawings.

Means for Solving the Problems

The typical ones of the inventions disclosed in the present application will be briefly described as follows.

More specifically, a summary of a typical invention includes: first illuminating means for coherently illuminating from a direction tilted to a normal line of a sample with a laser as a light source; second illuminating means illuminating incoherent light having a wavelength different from that of the first illuminating means; a detecting system capturing scattered light from the sample; and a spatial filter arranged on at least one of detecting light paths divided (branched) in accordance with the first illuminating means and the second illuminating means in the detecting system and shielding a part of the scattered light from the sample, the invention determining a defect candidate based on the scattered light transmitted through the spatial filter.

BRIEF DESCRIPTION OF THE DRAWINGS

FIG. 2A is an explanatory diagram for describing scattered light in the device of inspecting defects according to the first embodiment of the present invention;

FIG. 2B is an explanatory diagram for describing scattered light in the device of inspecting defects according to the first embodiment of the present invention;

FIG. 7 is a configuration diagram illustrating a configuration of an illumination optical system of the device of inspecting defects according to the third embodiment of the present invention;

FIG. 8A is a diagram illustrating a configuration of a MEMS mirror array of the device of inspecting defects according to the third embodiment of the present invention;

FIG. 8B is a diagram illustrating a configuration of the MEMS mirror array of the device of inspecting defects according to the third embodiment of the present invention.

DESCRIPTION OF THE PREFERRED EMBODIMENT

Effects of the Invention

The effects obtained by typical aspects of the present invention will be briefly described below.

That is, an effect achieved by the typical invention is obtaining an image, in which defects are signified, being advantageous in increasing sensitivity by efficiently detecting scattered light from a defect to be inspected with properly shielding scattered light and diffracted light from various kinds of normal patterns existing on a wafer.

Also, when intensity of illumination light is increased for ensuring scattered light of a minute defect, it is possible to reduce brightness saturation in a normal pattern image having a large amount of scattered light, and thus it is possible to improve capture efficiency of defects.

Hereinafter, embodiments of the present invention will be described in detail with reference to the accompanying drawings. Note that components having the same function are denoted by the same reference symbols throughout the drawings for describing the embodiment, and the repetitive description thereof will be omitted.

First Embodiment

Figure 1:
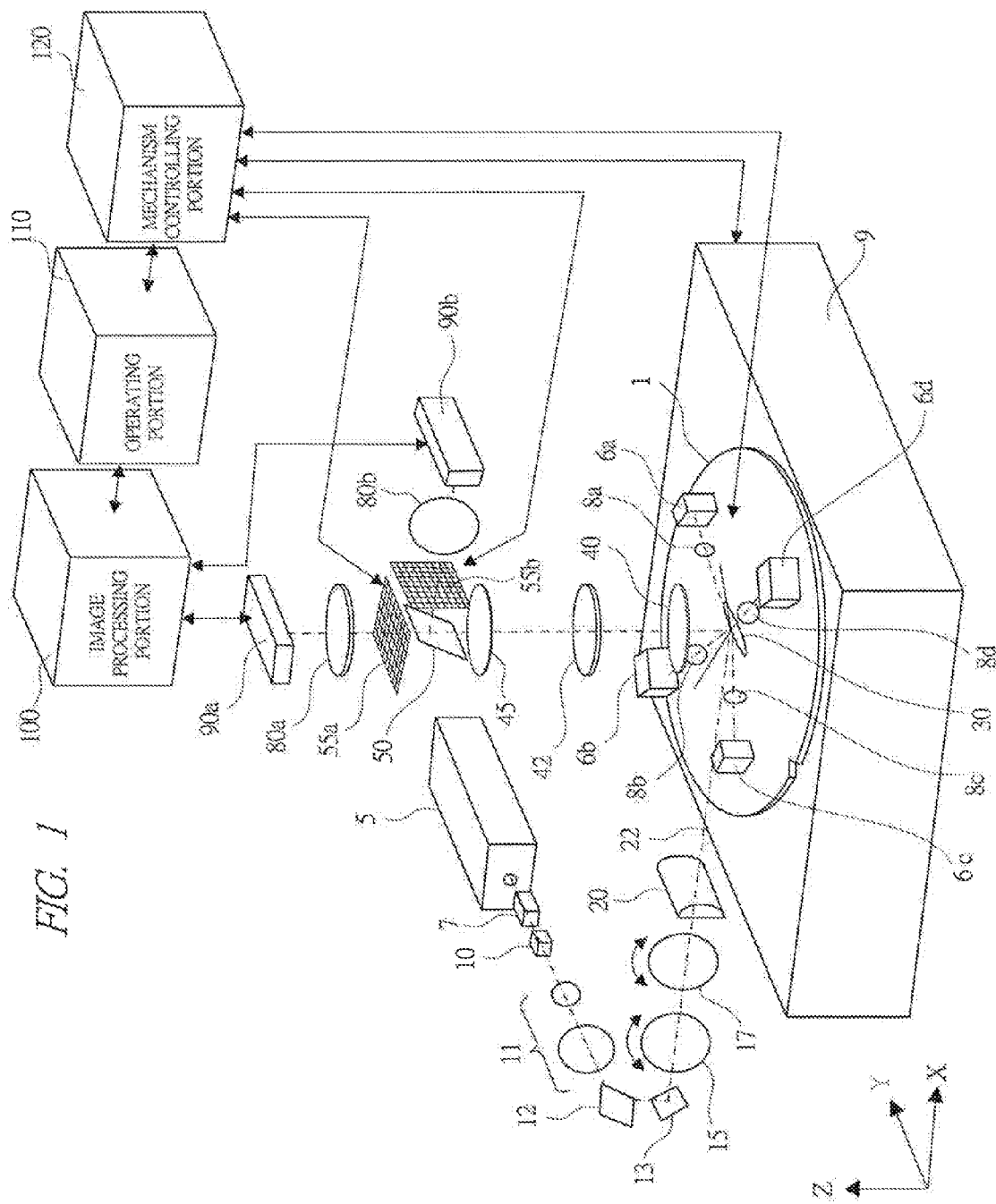
FIG. 1 is a configuration diagram illustrating a configuration of a device of inspecting defects according to a first embodiment of the present invention.
Figure 3:
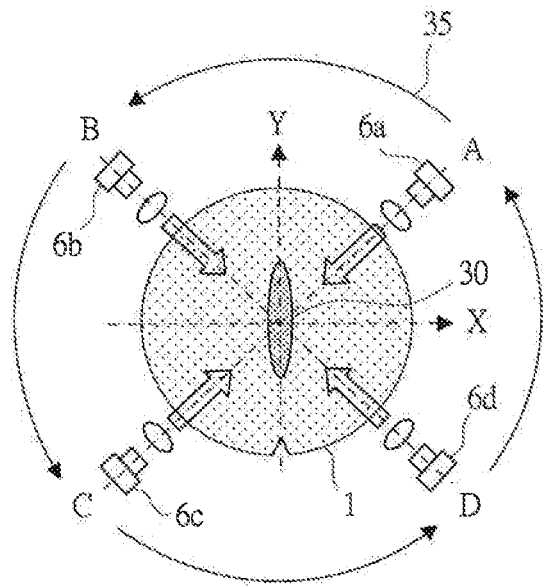
FIG. 3 is an explanatory diagram for describing rotating flash lamp illumination in the device of inspecting defects according to the first embodiment of the present invention.

With reference to FIGS. 1 to 4D, a configuration and an operation of a device of inspecting defects according to a first embodiment of the present invention will be described. FIG. 1 is a configuration diagram illustrating a configuration of a device of inspecting defects according to a first embodiment of the present invention; FIGS. 2A and 2B are explanatory diagrams for describing scattered light in the device of inspecting defects according to the first embodiment of the present invention; FIG. 3 is an explanatory diagram for describing rotating flash lamp illumination in the device of inspecting defects according to the first embodiment of the present invention; and FIGS. 4A to 4D are explanatory diagrams for describing a light-shielding pattern of a spatial modulation element in the device of inspecting defects according to the first embodiment of the present invention.

In FIG. 1, the device of inspecting defects is formed of: an illumination optical system including an XYZθ stage 9 on which a wafer 1 is mounted, a laser 5, an electric optical element 7, a PBS (Polarizing Beam Splitter) 10, a beam expander 11, mirrors 12 and 13, a half-wavelength plate 15, a quarter-wavelength plate 17, and a cylindrical lens 20; an incoherent illumination system having LEDs (Light Emitting Diodes) 6a, 6b, 6c and 6d and lenses 8a, 8b, 8c and 8d; and a detection optical system including an objective lens 40, lenses 42 and 45, a dichroic mirror 50, spatial modulation elements 55a and 55b, imaging lenses 80a and 80b, image sensors 90a and 90b; an image processing portion 100; an operating portion 110; and a mechanism controlling portion 120.

The wafer 1 is mounted on the XYZθ stage 9 and a θ-alignment in a stage scanning direction is performed with respect to a pattern formed on the wafer 1. A dark-field image of the wafer 1 is detected by continuously detecting an image of scattered light with scanning the XYZθ stage 9 in an X direction at a constant speed.

The illumination optical system is arranged in a tilted direction to the wafer 1 and linearly illuminates 30 the wafer 1. A light source used in the illumination optical system is the laser 5, and candidates of an oscillation wavelength λ1 are DUV (Deep Ultraviolet) light to visible light such as a 532-nm laser of YAG second harmonic, a third-harmonic 355-nm or fourth-harmonic 266-nm laser, and a 199-nm laser.

Also, a multi-wavelength laser oscillating multiple wavelengths and a lamp are candidates. Candidates of the lamp are a mercury lamp and a mercury xenon lamp emitting d line (588 nm), e line (546 nm), g (436 nm), h (405 nm), and i line (365 nm).

Laser light 22 obtained by oscillating the laser 5 enters the electric optical element 7 (such as $LiNbO_3$ and PLZT [abbreviation of (Pb, La) (Zr, Ti)$O_3$]) which electrically controls polarized light in a predetermined direction. Instead of the electric optical element 7, a magnetic optical element formed of, for example, a garnet film may be used.

By controlling the polarizing direction, light to be transmitted through the PBS (Polarizing Beam Splitter) 10 is reduced to a predetermined amount, and entered to the beam expander 11 to enlarge a beam diameter.

The beam is reflected to the wafer 1 side at the mirrors 12 and 13, and set to a predetermined polarized state at the half-wavelength plate 15 and the quarter-wavelength plate 17.

For example, to the wafer 1, there are S polarization, P polarization, and alternatively, linear polarization or clockwise or anticlockwise ellipsoidal (circular) polarization oscillating at an angle in the midst between S polarization and P polarization. The cylindrical lens 20 is arranged so that an illuminating range by the laser light 22 on the wafer 1 is thin-line illumination being thin in the X direction and longitudinal in a Y direction.

As the other illumination system, the incoherent illumination system is arranged. For the incoherent light (λ2), a light source having a different wavelength than that of the coherent light (λ1) of the laser 5 are included. In the example of the present embodiment, four LEDs 6a, 6b, 6c and 6d are provided. Each LED of 6a, 6b, 6c and 6d is arranged in an azimuth direction at an angle of about 45 degrees to the X and Y directions when viewing the wafer 1 in a plane from a Z axis.

Light emitted from these LEDs 6a, 6b, 6c and 6d is incoherent light having a specific wavelength width and there is an effect of lowering spatial coherence by disposing a plurality of LEDs.

Each emitted light from the LEDs 6a, 6b, 6c and 6d in four azimuth directions is illuminated in a line shape on the wafer 1 by the lens 8a, 8b, 8c or 8d arranged in a light path.

Among light scattered by the patterns or defects on the wafer 1, light propagated in NA (Numerical Aperture) of the objective lens 40 is captured by the objective lens 40 and led to the detection optical system.

The lenses 42 and 25 and the dichroic mirror 50 are arranged in the detection optical system. An image being conjugate to a pupil (Fourier transform plane) of the objective lens is formed in each of optical paths divided (branched) to the coherent light (λ1) and the incoherent light (λ2) by the dichroic mirror 50. The spatial modulation elements 55a and 55b are arranged at respective pupil image positions to shield specific scattered light and diffracted light.

Light transmitted through the spatial modulation elements 55a and 55b forms a scattered image on each of the image sensors 90a and 90b at the imaging lenses 80a and 80b. Images detected by the image sensors 90a and 90b are inputted to the image processing portion 100 and defects are detected by a comparison processing with an image (for example, an image of an adjacent die) on the same pattern in design.

Information such as coordinates of a detected defect, a size and brightness is sent to the operating portion 110 and it is possible for a user of the device of inspecting defects to display defect information such as a defect map on the wafer and output defect information data.

Also, the operating portion 110 has a function of performing operation instruction of the device of inspecting defects, and instructs the mechanism controlling portion 120 to operate and controls operation of the XYZθ stage 9 and optical parts from the mechanism controlling portion 120.

As the spatial modulation elements 55a and 55b used in the detection optical system, there are a micro shutter array and a liquid crystal filter utilizing electrooptical effects of a birefringent element (such as $LiNbO_3$ and PLZT [abbreviation of (Pb, La) (Zr, Ti) $O_3$]) and a filter in one-dimensional and two-dimensional array using MEMS (Micro Electro Mechanical Systems).

Since transmission and shielding of light can be switched at a high speed by electric control in these devices, it is possible to change to a proper filtering pattern during an inspection in accordance with a pitch and a shape of a pattern 3 on the wafer 1.

Also, to match a surface layer of the wafer 1 with a focus point position of the objective lens 40, it is necessary to control a height of the wafer 1 by the XYZθ stage 9. As a method of detecting the wafer height, there is, for example, an optical lever method providing an illumination system for height detection which illuminates slit light to the wafer and a wafer height detecting portion for obtaining a height of the wafer from a position of a slit image by detecting slit light reflected on the wafer 1.

When there is an unallowable defocusing as a difference between the height of the wafer and the focus position of the objective lens 40 is obtained, the mechanism controlling portion 120 issues an instruction to the XYZθ stage 9 to align the wafer 1 to the focus point.

According to the configuration described above, while defects on the wafer 1 are detected, a logic computing portion on an LSI generally has non-cyclic patterns formed thereto. The non-cyclic patterns are formed of perpendicularly crossing wirings and formed in a direction parallel (or perpendicular) to a line of dies formed on the wafer 1.

In the example illustrated in FIG. 1, the direction in which dies are aligned is taken as the scanning direction X of the XYZθ stage 9, and thus wirings of main logic patterns are in the X and Y directions.

A cross sectional structure of the wafer 1 is illustrated in FIG. 2A. A logic pattern 3a longitudinal in the X direction and a logic pattern 3b longitudinal in the Y direction are formed to the surface of the wafer 1. To schematically illustrate scattered light from these patterns, a hemisphere is assumed to be on the wafer 1.

A plan view is illustrated in FIG. 2B where intensity of light reached to the hemisphere is viewed from above the hemisphere to the wafer 1 assuming that scattered light from these patterns reaches the hemisphere when illuminating the wafer 1. In FIG. 2B, light positioned in a circle at the outermost periphery is light propagated in a direction horizontal to the wafer.

Also, a position corresponding to the NA (Numerical Aperture) of the objective lens 40 is a circle 39. Therefore, light scattered to the inside than the circle 39 is captured by the objective lens 40. When illumination light is positioned at 34 in FIG. 2B, regular reflection light 37 regularly reflected on the wafer 1 reaches a position symmetry with respect to a point about an optical axis.

In this case, scattered light from the patterns 3a and 3b in the X and Y azimuth directions is distributed in the Y and X directions having the regular reflection light 37 as a crossing point in FIG. 2B. This situation is schematically illustrated by 32 and 33 in FIG. 2B.

As the scattered light contains a lot of noise components which inhibit sensitivity in defect inspection, the scattered light of the logic patterns is shielded in the range illustrated by 36 in FIG. 2B, thereby improving inspection sensitivity.

As the spatial modulation element shielding the pattern scattered light, a device such as a shutter array in which elements with controlled light shielding and transmission are aligned in two-dimensional form is effective. However, shielding light by a spatial modulation element limits an aperture of the objective lens 40. Therefore, when illuminating from an azimuth direction at 45 degrees to the X and Y axes at the same time, the aperture of the objective lens 40 becomes smaller and it causes an inhabitation of resolving power the objective lens 40 has.

As a countermeasure to that, as illustrated in FIG. 3, illumination having lowering of resolving power of the objective lens 40 being suppressed by temporally dividing illumination from four azimuth directions at 45 degrees is used.

The illuminations from four azimuth directions are taken as flash light illumination with temporal differences, respectively. As to illuminating positions, each of the LEDs 6a, 6b, 6c and 6d commonly illuminates the same position on the wafer 1. Temporal emitting timing is such that the LED 6a is turned on at a time A and light of the other LEDs 6b, 6c and 6d is turned on or shielded not to let light reach the wafer 1. At a next time B, the LED to be turned on is changed in the direction of an arrow 35. In the case of the time B, only the LED 6b is turned on. By sequentially polarizing light of the LEDs turned on in this manner, it is possible to achieve flash light illumination with sequentially shifted azimuth directions of illumination.

A shape of the spatial modulation element which shields light of the logic pattern scattered light corresponding to the rotating flash light illumination illustrated in FIG. 3 and the illuminations from respective azimuth directions are illustrated in FIGS. 4A to 4D. FIGS. 4A to 4D illustrates a light-shielding pattern corresponding to the illumination azimuth directions of the time A, B, C and D in FIG. 3.

Figure 4A:
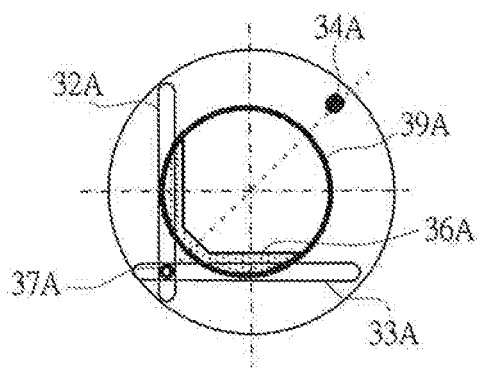
FIG. 4A is an explanatory diagram for describing a light-shielding pattern of a spatial modulation element in the device of inspecting defects according to the first embodiment of the present invention.

FIG. 4A is alight shielding pattern corresponding to the time A in FIG. 3 and expression of FIG. 4A is in the same manner as FIG. 2B.

In the case of the illumination light 34A, regular reflection light reaches 37A. Scattered light from the pattern longitudinal in the X direction is distributed in the region of 32A. Also, light from the Y-direction pattern is distributed in 33A.

Spatial modulation elements capable of controlling transmission and light shielding are arranged in a two-dimensional form to shield light from the regions 32A and 33A in which the pattern scattered light is strongly distributed by the pattern denoted by 36A.

Figure 4C:
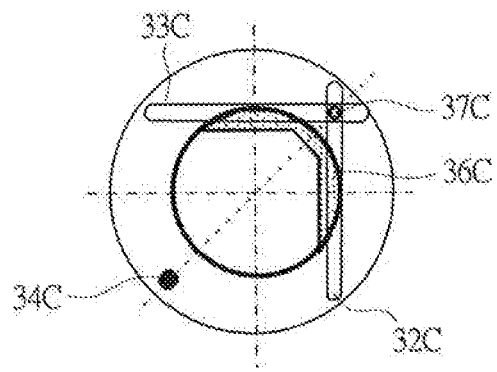
FIG. 4C is an explanatory diagram for describing the light-shielding pattern of a spatial modulation element in the device of inspecting defects according to the first embodiment of the present invention.
Figure 4B:
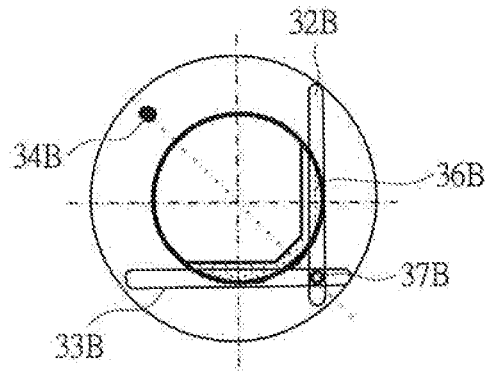
FIG. 4B is an explanatory diagram for describing a light-shielding pattern of a spatial modulation element in the device of inspecting defects according to the first embodiment of the present invention.

At the next time B illustrated in FIG. 4B, the regular reflection light reaches 37B. At this moment, the light-shielding pattern is set to 36B.

Figure 4D:
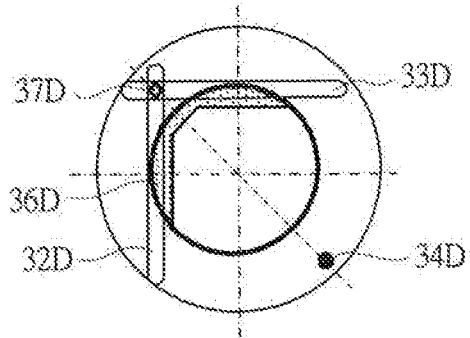
FIG. 4D is an explanatory diagram for describing the light-shielding pattern of a spatial modulation element in the device of inspecting defects according to the first embodiment of the present invention.

In the same manner, light-shielding patterns of the spatial modulation elements are set to 36C and 36D respectively to the time C illustrated in FIG. 4C and the time D illustrated in FIG. 4D. In this manner, as a light-shielding portion is an overlap of 36A, 36B, 36C and 36D in FIGS. 4A to 4D in simultaneous illumination, the aperture is narrow but it is possible to shield light only in a region having a lot of inspection noise at the time A, B, C and D according to the operation described above, and it is possible to suppress lowering of resolving power of the objective lens 40 due to unnecessary shielding.

Second Embodiment

While LEDs have been used as light source in the incoherent illumination optical system in the first embodiment, a second embodiment uses another light source.

Figure 5A:
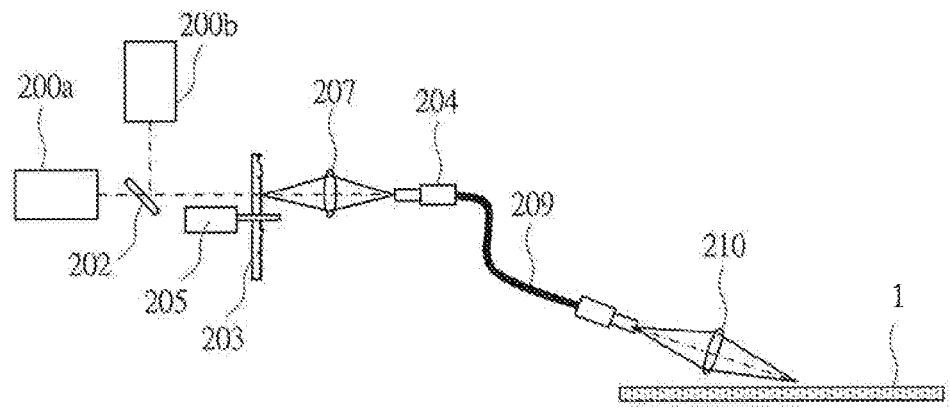
FIG. 5A is a configuration diagram illustrating a configuration of an incoherent illumination optical system of a device of inspecting defects according to a second embodiment of the present invention.
Figure 5B:
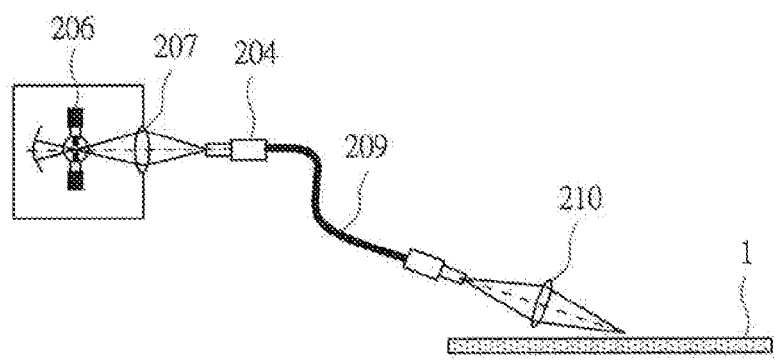
FIG. 5B is a configuration diagram illustrating the configuration of the incoherent illumination optical system of the device of inspecting defects according to the second embodiment of the present invention.

With reference to FIGS. 5A and 5B, a configuration of an incoherent illumination optical system of a device of inspecting defects according to the second embodiment will be described. FIGS. 5A and 5B are configuration diagrams illustrating the configuration of an incoherent illumination optical system of the device of inspecting defects according to the second embodiment, and the other configurations are the same as the first embodiment.

FIG. 5A is an example of a configuration using two lasers. Two lasers 200a (wavelength: λ2a) and 200b (wavelength: λ2b) having different wavelengths are used as light sources, and they are led to a common illumination light path by a dichroic mirror 202.

To temporally diffuse aligned phases of the laser beams (λ2a) and (λ2b) at the common light path, the laser beams are entered to a rotating diffusion plate 203 attached to a motor 205. At the rotating diffusion plate 203, the phases are temporally disturbed by minute concavity and convexity (grains) on the diffusion plate. These light beams are collected by a lens 207, and an incidence end 204 of a fiber is arranged at the light-collecting position. A lens 210 is arranged on an output end side of the fiber to illuminate the wafer 1.

Further, FIG. 5B is an example of a configuration using a lamp as a light source. Candidates of a lamp 206 are a mercury lamp and a mercury xenon lamp emitting d line (588 nm), e line (546 nm), g (436 nm), h (405 nm), and i line (365 nm), and, as light from the lamp 206 is incoherent light, the emitted light is collected by the lens 207 as it is and entered to the incident end 204 of the fiber 209. A lens 210 is provided on the output side of the fiber 209 to illuminate the wafer 1.

In the configuration illustrated in FIGS. 5A and 5B, an example of one azimuth direction is schematically illustrated among the four azimuth directions illustrated in FIG. 1 but it may not be four systems but one system in practice and it is not necessarily azimuth directions at 45 degrees.

As an example, there is no problem in arranging LEDs and the illumination system illustrated in FIGS. 5A and 5B in all azimuth directions. An effect achieved by the incoherent illumination is aimed at stably detecting an image of light scattered by a pattern which the spatial modulation element 55b failed to shield.

This stable detection suppresses ripple of a pattern edge image due to coherent illumination, variations in a pattern image due to variations in thickness of an oxide film on the wafer 1, and variations in brightness (noise component upon inspection) of a normal pattern, which is not a defect, due to differences in brightness etc. posed by minute shape differences in the pattern not critical to operation of semiconductor circuits, thereby improving inspection sensitivity.

Third Embodiment

A third embodiment is a method of illumination with reduced coherency of the laser beam of the illumination optical system in the first embodiment.

Figure 6:
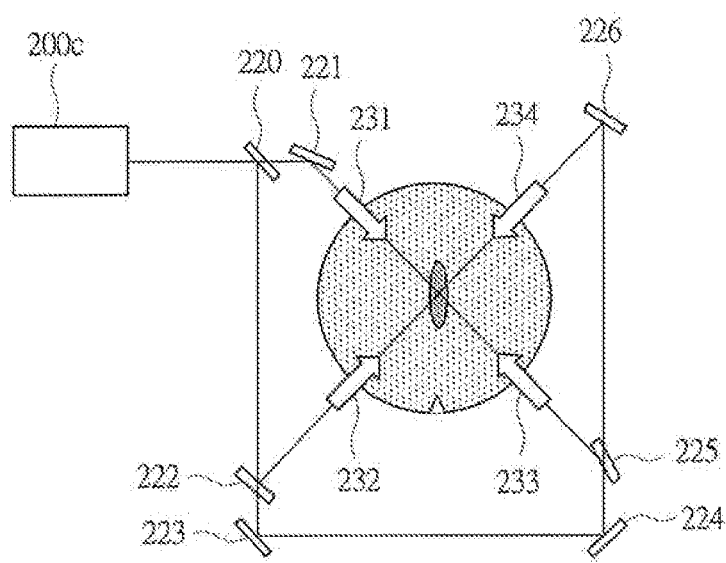
FIG. 6 is a configuration diagram illustrating a configuration of an illumination optical system of a device of inspecting defects according to a third embodiment of the present invention.

With reference to FIGS. 6 to 8B, a configuration of an illumination optical system of a device of inspecting defects according to the third embodiment of the present invention will be described. FIGS. 6 and 7 are configuration diagrams illustrating the configuration of the illumination optical system of the device of inspecting defects according to the third embodiment, and FIGS. 8A and 8B are diagrams illustrating a structure of a MEMS mirror array of the device of inspecting defects according to the third embodiment of the present invention. The other configurations are the same as the first embodiment.

First, in the example of a method of illumination illustrated in FIG. 6, light from a laser 200c is divided (branched) at a first stage at a partial mirror 220. The partial mirror 220 is made to have a dividing ratio of 1 (transmission):3 (reflection).

Transmitted light illuminates 231 the wafer 1 by a mirror 221. Reflected light is divided at a second stage at a partial mirror 222, and a dividing ratio is set to 1 (reflection):2 (transmission). Light reflected at the partial mirror 222 illuminates 232 the wafer 1.

The light transmitted through the partial mirror 222 is transmitted through mirrors 223 and 224 and divided at a third stage at a partial mirror 225. Light reflected at the partial mirror 225 illuminates 233 the wafer 1.

Further, the light transmitted through the partial mirror 225 is reflected at a mirror 226 and illuminates 234 the wafer 1. Illuminations 231, 232, 233 and 234 divided to four light paths are arranged to have respective optical path differences longer than or equal to a coherence length of light oscillating the laser 200c. In this manner, as the interference of light illuminated from respective directions is suppressed, and thus there is an effect in stable detection of scattered light from normal patterns.

In addition, while the example illustrated in FIG. 6 is a method of stably detecting a pattern using light path differences longer than or equal to a coherent length with using a laser beam, in addition to that, a method of illumination using a method of temporally disturbing phases of laser beams is illustrated in FIG. 7.

In the example of the method of illumination illustrated in FIG. 7, a laser beam obtained by oscillating a laser 200d has a beam diameter enlarged by lenses 235 and 236 and entered into a MEMS mirror 250. To a surface of the MEMS mirror 250, mirrors being individually drivable are arranged in a two-dimensional form. The mirror array has individual mirrors independently drivable and phase of the laser beam is temporally disturbed to temporally changing a wavefront from 253, 252 to 251.

The light having a temporally disturbed wavefront illuminates the wafer 1 by a lens 254. In this manner, scattered light from patterns is stably detected. The scattered light detecting system images a scattered image on an image sensor 90a by the objective lens 40 and the lens 45.

A cross sectional structure of the MEMS mirror 250 is illustrated in FIGS. 8A and 8B. The MEMS mirror 250 has a plurality of micro mirrors 262a, 262b, 262c, . . . aligned in a two-dimensional form on a Si substrate 260, and, in a case of not disturbing phases, surfaces of the micro mirrors 262a, 262b, 262c, . . . are fixed at a certain height as illustrated in FIG. 8A.

On the contrary, to temporally disturb phases, individual micro mirrors 262a, 262b, 262c, . . . are randomly moved vertically, for example, as illustrated in FIG. 8B. In this manner, reflected light has temporally changed disturb of a wavefront. A cycle of disturbing the wavefront is at least faster than an accumulation time of an image sensor and thus it is possible to detect a stable pattern image.

Note that the illumination optical system of the present embodiment may be uses as the incoherent optical system of the illumination optical system of the first embodiment.

Fourth Embodiment

In a fourth embodiment, two image sensors are used in both of the illumination optical system and the incoherent illumination optical system in the first embodiment to perform an alignment processing.

Figure 9:
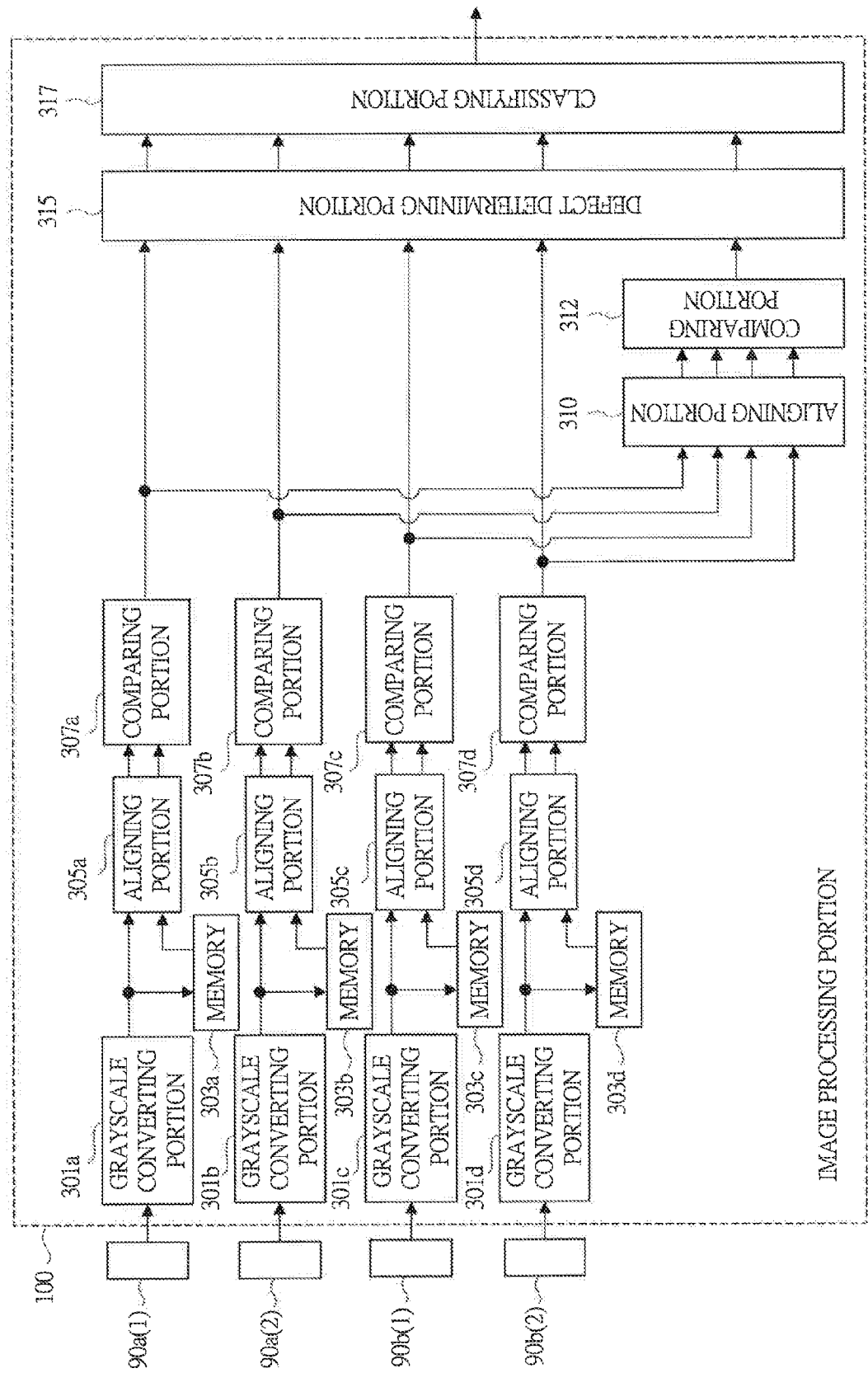
FIG. 9 is a configuration diagram illustrating a configuration of an image processing portion of a device of inspecting defects according to a fourth embodiment of the present invention.

With reference to FIG. 9, a processing of an image processing portion of a device of inspecting defects according to the fourth embodiment will be described. FIG. 9 is a configuration diagram illustrating a configuration of the device of inspecting defects according to the fourth embodiment of the present invention.

In FIG. 9, as the image sensor, image sensors 90a(1), 90a(2) for the illumination optical system, and image sensors 90b(1) and 90b(2) for the incoherent illumination optical system are provided.

In addition, output signals of the image sensors 90a(1), 90a(2), 90b(1) and 90b(2) are inputted to the image processing unit 100.

Images detected at the image sensor 90a(1) are subjected to conversion of brightness such as γ correction in a grayscale converting portion 301a. One of images after conversion is sent to an aligning portion 305a and the other is sent to a memory 303a. In the aligning portion 305a, an image stored in and sent from the memory 303a is aligned until it becomes the same pattern (for example, an adjacent die) with an image already sent.

In a comparing portion 307a, a comparing processing of a differential image of two images being aligned is performed to calculate an amount of characteristic as a result of the comparison. Defects are determined in a defect determining portion 315 using the amount of characteristic (for example, the maximum value of contrast and size).

The sequence of processings is also performed in the same manner as to each of the image sensors 90a(2), 90b(1) and 90b(2).

Further, a result of comparison of each image is sent to an aligning portion 310 and polarization and alignment of four images having different wavelengths are performed to compare amounts of characteristic in different optical conditions so that defects are determined by sending the amounts of characteristic to the defect determining portion 315.

While a determination is performed using five kinds of amounts of characteristic in the defect determining portion 315, when it is determined that there is a defect in any of determination results, the amount of characteristic is sent to a classifying portion 317 together with the remaining four kinds of amounts of characteristic.

In the classifying portion 317, types of defects (for example, foreign substance, residue of etching, scratch) and pseudo defects (such as unevenness of brightness of an oxide film not critical to the device, roughness of patterns, and grains) are classified and coordinates of defects, classification results, and amounts of characteristic, etc. are outputted.

By detecting defects in this manner, it is possible to detect defects more accurately.

In the foregoing, the invention made by the inventors of the present invention has been concretely described based on the embodiments. However, it is needless to say that the present invention is not limited to the foregoing embodiments and various modifications and alterations can be made within the scope of the present invention.

INDUSTRIAL APPLICABILITY

The present invention is widely applicable to a device and a system for detecting defects of fine patterns formed on a wafer and foreign substance.

DESCRIPTION OF REFERENCES

1 . . . Wafer, 3a and 3b . . . Pattern, 4 . . . Defect, 5 . . . Laser, 6a, 6b, 6c and 6d . . . LED, 7 . . . Electric optical element, 8a, 8b, 8c and 8d . . . Lens, 9 . . . XYZθ stage, 10 . . . PBS, 11 . . . Beam expander, 12 and 13 . . . Mirror, 15 . . . Half-wavelength plate, 17 . . . Quarter-wavelength plate, 20 . . . Cylindrical lens, 22 . . . Laser beam, 30 . . . Illuminated region, 40 . . . Objective lens, 42 and 45 . . . Lens, 43 . . . Half-wavelength plate with rotating mechanism, 44 . . . Quarter-wavelength plate with rotating mechanism, 50 . . . Dichroic Mirror, 55a and 55b . . . Spatial modulation element, 80a and 80b . . . Imaging lens, 90a and 90b . . . Image sensor, 100 . . . Image processing portion, 110 . . . Operating portion, 120 . . . Mechanism controlling portion, 130 . . . Height detecting portion, 200a, 200b, 200c and 200d . . . Laser, 202 . . . Dichroic Mirror, 203 . . . Rotating diffuser plate, 204 . . . Incident end, 205 . . . Motor, 206 . . . Lamp, 207 . . . Lens, 209 . . . Fiber, 210 . . . Lens, 220, 222 and 225 . . . Partial Mirror, 221, 223, 224 and 226 . . . Mirror, 235 and 236 . . . Lens, 250 . . . MEMS Mirror, 254 . . . Lens, 262a, 262b and 262c . . . Micro Mirror, 301a, 301b, 301c and 301d . . . Grayscale converting portion, 303a, 303b, 303c and 303d . . . Memory, 305a, 305b, 305c and 305d . . . Aligning portion, 307a, 307b, 307c and 307d . . . Comparing portion, 310 . . . Aligning portion, 312 . . . Comparing portion, 315 . . . Defect determining portion, and 317 . . . Classifying portion.

The invention claimed is:
1. A method of inspecting defects of detecting defects of a sample to which a circuit pattern is formed, the method comprising:
 a scanning step of scanning the sample;
 an illuminating step of illuminating in a plurality of illumination azimuth directions, from an angle tilted to a normal direction with respect to a surface of the sample;
 a light-shielding step of shielding a portion of the scattered light scattered from the surface of the sample, by use of a spatial filter arranged on at least one detecting light path, the scattered light resulting from the illuminating step;
 a detecting step including an imaging step of imaging the scattered light transmitted through the spatial filter arranged on at least one detecting light path; and
 a processing step of processing a comparison of signals based on the scattered light images in the imaging step;
 wherein illumination is performed with sequentially changing azimuth directions, by periodically shifting the illumination in the plurality of azimuth directions, and light-shielding patterns of the spatial filter are changed to shield lights of regular reflection in synchronization with the illumination.

2. The method of inspecting defects according to claim 1, wherein,
in the illuminating step, light having different wavelengths is transmitted as a mixture of coherent light and incoherent light.

3. The method of inspecting defects according to claim 1, wherein,
in the illuminating step, a wavefront in a flux of light of coherent light is temporally fluctuated by a temporally fluctuating wavefront unit.

4. The method of inspecting defects according to claim 3, wherein,
the temporally fluctuating wavefront unit includes a liquid crystal, an electric optical element, a magnetic optical element, or a MEMS.

5. A defect inspecting device for detecting defects of a sample to which a circuit pattern is formed, the device comprising:
an illuminating unit configured to illuminate in a plurality of illumination azimuth directions, from a tilted direction to a normal direction of a surface of the sample with using a laser as a light source;
a detecting unit, including a spatial filter arranged on at least one of detecting light paths of scattered light scattered from the surface of the sample, the spatial filter configured to shield a portion of the scattered light scattered from the sample, and an image sensor provided to each of the detecting light paths, and imaging the scattered light transmitted through the spatial filter; and
an image processing portion configured to process a comparison of signals based on the scattered light imaged by the image sensor and determining a defect candidate of the sample;
wherein illumination is performed with sequentially changing azimuth directions, by periodically shifting the illumination in the plurality of azimuth directions, and light-shielding patterns of the spatial filter are changed to shield lights of regular reflection in synchronization with the illumination.

6. The defect inspecting device according to claim 5,
wherein the second illuminating unit is configured to illuminate the sample after subjecting light to a temporal phase modulation, by using a laser as a light source, the spatial filter including a MEMS device in which micro mirrors are arranged in a two-dimensional form as unit configured to temporally modulate phases.

7. The defect inspecting device according to claim 5,
wherein the spatial filter includes a MEMS shutter array in which a plurality of shutters are arranged in a two-dimensional form.

8. The defect inspecting device according to claim 5, further comprising:
a stage configured to scan the sample in a horizontal plane.

* * * * *